(12) United States Patent
Lee

(10) Patent No.: US 6,334,737 B1
(45) Date of Patent: Jan. 1, 2002

(54) METHOD AND APPARATUS OF CONTROLLING LANDFILL GAS GENERATION WITHIN LANDFILL

(76) Inventor: Keum Young Lee, 3409-9, Kaebong3-Dong, Kuro-Ku, Seoul (KR)

( * ) Notice: Subject to any disclaimer, the term of this patent is extended or adjusted under 35 U.S.C. 154(b) by 0 days.

(21) Appl. No.: 09/465,759

(22) Filed: Dec. 17, 1999

(30) Foreign Application Priority Data

Dec. 23, 1998 (KR) .................................. 98-57487

(51) Int. Cl.[7] ....................................... B09B 1/00
(52) U.S. Cl. ................... 405/129.5; 405/129.95; 405/129.85; 405/129.45; 210/747; 210/170
(58) Field of Search ........................... 405/128, 129, 405/129.95, 129.85, 129.7, 129.57, 129.5, 129.45; 210/747, 170; 588/251

(56) References Cited

U.S. PATENT DOCUMENTS

| | | | |
|---|---|---|---|
| 4,252,462 A | * 2/1981 | Klingle et al. | 405/129 |
| 4,670,148 A | * 6/1987 | Schneider | 405/129 |
| 5,178,491 A | * 1/1993 | Graves et al. | 405/128 |
| 5,286,140 A | * 2/1994 | Mather | 405/128 |
| 5,562,586 A | * 10/1996 | Hyde-Smith | 405/129 |
| 5,564,862 A | * 10/1996 | Markels, Jr. | 405/129 |
| 5,605,417 A | 2/1997 | Englert et al. | |
| 5,857,807 A | * 1/1999 | Longo, Sr. | 405/129 |
| 5,888,022 A | * 3/1999 | Green | 405/129 |
| 6,024,513 A | * 2/2000 | Hudgins et al. | 405/129 |

FOREIGN PATENT DOCUMENTS

| | | |
|---|---|---|
| EP | 245796 | * 11/1987 |
| EP | 363508 | * 4/1990 |
| WO | 98/08628 | * 3/1998 |
| WO | WO 98/18576 | 5/1998 |

* cited by examiner

*Primary Examiner*—David Bagnell
*Assistant Examiner*—Frederick L. Lagman
(74) *Attorney, Agent, or Firm*—Jacobson Holman, PLLC

(57) ABSTRACT

Disclosed herein is a method of controlling the landfill gas generation within the landfill in which leachate is recycled to be continuously injected into a deposit of wastes while extracting the landfill gas from a landfill gas extraction pipe inserted into the waste deposit, comprising steps of:

(a) maintaining the recycling leachate at the temperature range of 35° C. to 38° C. and/or the pH of 6.5 to 7.5 until the amount of generated landfill gas reaches from the range of 5% to 20% of a capability of the landfill gas generation in the landfill; (b) maintaining the recycling leachate at the temperature range of 30° C. to 35° C. or the range of 60° C. to 65° C. and/or the pH of 6 to 7 until the amount of generated landfill gas reaches from the range of 75% to 90% of a capability of the landfill gas generation in the landfill; and (c) maintaining the recycling leachate at the temperature range of 35° C. to 38° C. or the range of 50° C. to 54° C. and/or the pH of 6.5 to 8.0 until the amount of generated landfill gas reaches to 100% of a capability of the landfill gas generation in the landfill.

20 Claims, 7 Drawing Sheets

METHOD AND APPARATUS OF CONTROLLING LANDFILL GAS GENERATION WITHIN LANDFILL

TECHNICAL FIELD

The present invention relates in general to a method and apparatus for controlling the amount of landfill gas generated within a landfill. More particularly, the present invention relates to a method and apparatus for controlling the amount of landfill gas generated within a landfill, capable of increasing a utilization efficiency of the methane gas resource to a maximum and stabilizing the landfill over a short period of time. These results are achieved by the appropriate control of the generation rate of the landfill gas containing methane generated continuously during the landfilling, degradation and stabilization processes of wastes as a main component.

BACKGROUND ART

Recently, with a rise in the standard of living, the generation of wastes including industrial wastes and municipal solid wastes is trending toward an increase by geometric progression. These mass-generated wastes are mostly treated by landfilling and incineration, as there is no suitable way of treating the wastes.

However, such mass-landfilled wastes need to be degraded in short period so that the landfill can be used effectively. These landfilled wastes have always a risk as an environmental pollution source until the wastes are completely degraded to be stabilized after long periods of time have lapsed. In particular, due to the eruption of contaminants, such as heavy metal, contained in landfilled waste itself from the landfill, or the infiltration of rainwater into the landfill, leachate from the landfill act as a main factor contaminating the adjacent soils or streams.

Additionally, an excess of landfill gas is generated during the degradation process of a variety of organic material contained in the landfilled wastes. This landfill gas causes serious atmospheric pollution. As the landfill gas contains, as main components, methane and carbon dioxide, it results in a greenhouse effect upon the emission into the atmosphere. Thus, the landfill gas has a problem in that acts as a direct factor to abnormal climate phenomena such as the La Nina and El Nino.

In particular, in the case where the methane contained in the landfill gas is in the amount of 50 to 60%, it is negative in view of the environmental pollution as it has an influence on the greenhouse effect to a degree of 21 times or more compared to that of carbon dioxide. However, as methane is very excellent in combustion property, an efficient technology for collecting the landfill gas is keenly demanded if taking the resource utilization aspect into consideration. Furthermore, due to the oil shock which had been encountered throughout the world in the early 1970's, some advanced countries such as USA, Germany, etc. have begun to newly recognize, as a good quality resource, the landfill gas containing methane as its main component. At present, it has come to the stage of developing a technology put to practical use with a landfill gas treatment facility capable of collecting and treating the landfill gas by collection pipes disposed at one side of the landfill.

Generally, the landfills can be classified, depending on the landfilling method, into an anaerobic landfill, an anaerobic sanitary landfill in which a daily intermediate soil covering is carried out, a semi-aerobic landfill in which an apparatus for collection and delivery of water is disposed, and an aerobic landfill into which air can be injected. Among these landfills, the semi-aerobic landfill or the aerobic landfill is preferable in view of environmental consideration such as the generation of offensive odors, but the equipment and operation costs are excessive.

In the cases of the semi-aerobic landfill or the aerobic landfill, the content of methane, an anaerobic degradation product, in the landfill gas is relatively reduced. However, if a method capable of efficiently utilizing and controlling the landfill gas with time can be presented, the anaerobic sanitary landfill is preferable when considering all the environmental and economical aspects, such as the utilization of the waste resource. The amount of landfill gas generated with time within such landfills exhibits a great variation for each stage of a waste landfilling process, a waste post-landfilling process and a landfilling stabilization process, depending on a variety of factors such as the waste character, the landfilling method and the natural conditions. These stages have been generally progressing over a period of time for about 20 years. This landfill gas generation amount shows a maximum value at a point of time of about one year to three years after the completed landfilling, as shown in FIG. 3 showing a curve of landfill gas production rate in a common landfill.

Therefore, for an efficient extraction, collection, and utilization of an entire amount of the landfill gas generated within the landfill, a utilization facility involved needs to be designed and constructed with respect to a maximum generation amount of the landfill gas. However, such design and construction has many problems when considering the economical aspect, and thus can be applied only to the limited landfill facility of a special scale. As a result, only about 30% to 50% of the capable landfill gas generation in the landfill is utilized, and the remainder is incinerated or escaped into the atmosphere.

Taking such a problem into consideration, studies are progressing to artificially controll the anaerobic condition in the landfill at the landfilling process, thereby increasing a generation of the landfill gas. The activation of the anaerobic condition in the landfill also enables the landfill gas utilization facility to be designed at a reasonable capacity and to be used for an extended period of time, and also to be shortened in a recovery term of its investment cost. Typically, in Korean Patent Application No. 97-56300, there is disclosed a landfill process comprising the steps of landfilling wastes between vertically built banks, and graveling the wastes surface to enable the ventilation therethrough. The disclosed process further includes the subsequential steps of disposing pipelines for injecting leachate amid the gravel, covering the gravel with a sealing sheet at just slightly higher above the gravel, and then soil-covering.

In the above described patent application, the leachate effluent from the landfill is simply recycled to be injected into the final cover of the landfill. This is advantageous in that the amount of generated leachate is significantly reduced. Another advantage is in that an aerobic condition at an initial stage of the landfilling process is weakenened while activating the anaerobic condition, such that the amount of generated methane gas contained in the landfill gas at an initial stage of the landfilling process can be somewhat increased.

However, the technology described in the patent application is to facilitate the generation of methane at an initial stage of the landfilling process, depending only on the simple recycling of the leachate. Since, in the above application, there is no consideration for other factors facilitating gas generation such as pH and temperature within the landfill, it has a limitation in maintaining the amount of generated gas at a constant level throughout an entire duration of the landfilling process, the post-landfilling process and the landfilling stabilization process by suitably controlling a phenomenon in that the amount of the generated landfill gas is rapidly increased at the completed landfilling and is rapidly decreased at the landfilling stabilization process. Therefore, the above prior application is problematic in that it is difficult to determine the reasonable scale of the facility for utilizing landfill gas and also an efficiency for utilizing landfill gas is greatly decreased.

DISCLOSURE OF THE INVENTION

It is therefore an object of the present invention to provide a method and apparatus of controlling the amount of landfill gas generated within a landfill capable of designing facilities necessary for the recovery of the landfill gas, such as purification and power generation facilities, at a reasonable scale. This method and apparatus thus enables the cost of the investment in the facilities to be recovered over a short period of time, the utilization efficiency of the landfill gas resource to be maximized, and also the landfill to be stabilized over a short period of time. Such an object is achieved by suitably monitoring and controlling a variety of conditions of the recycling leachate for every stage of a landfilling process, a post-landfilling process and a landfilling stabilization process, such that the amount of the landfill gas generated is kept as constant as possible throughout all these processes.

BRIEF DESCRIPTION OF THE DRAWINGS

The foregoing and other objects, features and advantages of the invention will be apparent to those skilled in the art to which the present invention relates from reading the following specification with reference to the accompanying drawings, in which.

BEST MODE FOR CARRYING OUT THE INVENTION

In one embodiment, the present invention provides a method of controlling the rate of a landfill gas generation in a landfill, in which leachate is recycled to be continuous injected into a deposit of wastes while extracting the landfill gas from a landfill gas extraction pipe inserted into the waste deposit, comprising steps of:

(a) maintaining the recycling leachate at the temperature of 35° C. to 38° C. and/or the pH of 6.5 to 7.5 until the amount of the generated landfill gas reaches from the range of 5% to 20% of a capability of the landfill gas generation in the landfill;

(b) maintaining the recycling leachate at the temperature range of 30° C. to 35° C. or the range of 60° C. to 65° C. and/or the pH of 6 to 7 until the amount of the generated landfill gas reaches from the range of 75% to 90% of capability of the landfill gas generation in the landfill; and (c) maintaining the recycling leachate at the temperature of the range of 35° C. to 38° C. or the range of 50° C. to 54° C. and/or the pH of 6.5 to 8.0 until the amount of the generated landfill gas reaches 100% of capability of the landfill gas generation in the landfill.

Figure 3:
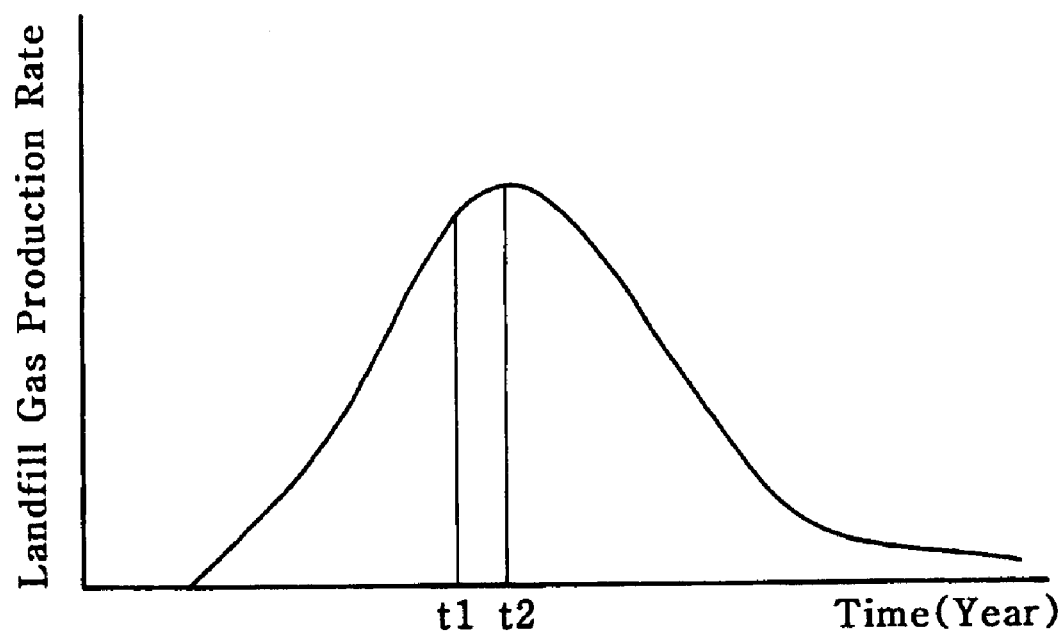
FIG. 3 is a curve showing the production rate of landfill gas generated within the general landfill.

As described already regarding FIG. 3, since the aerobic condition of the landfill, is maintained due to air drawn into the landfill, a carbon source is consumed for the production of carbon dioxide by the aerobic microbes, rather than for the production of methane. Therefore, the step (a) is to activate the production of methane by deriving the condition of the landfill gas production reaction at an initial stage of the landfilling process from the aerobic condition to the anaerobic condition. In the step (a), in order to dissipate almost all oxygen contained in the waste itself and also to prevent oxygen from percolating from the exterior, the leachate, being in a suitable condition for the methane generation, is continuously recycled and supplied to the landfill, thereby is facilitated anaerobic degradation of the waste within the landfill. Moreover, the amount of the methane contained in the landfill gas is highly increased.

As known in the art, when producing methane by the anaerobic decomposition of organic material, a generated amount of methane is determined depending on an activity of methane-producing bacteria, such as methanobacterium, methanobacillus, methanococcus, methanosarcina, and the like. This activity of the methane-producing bacteria is highly influenced by temperature and pH, etc.

Figure 4:
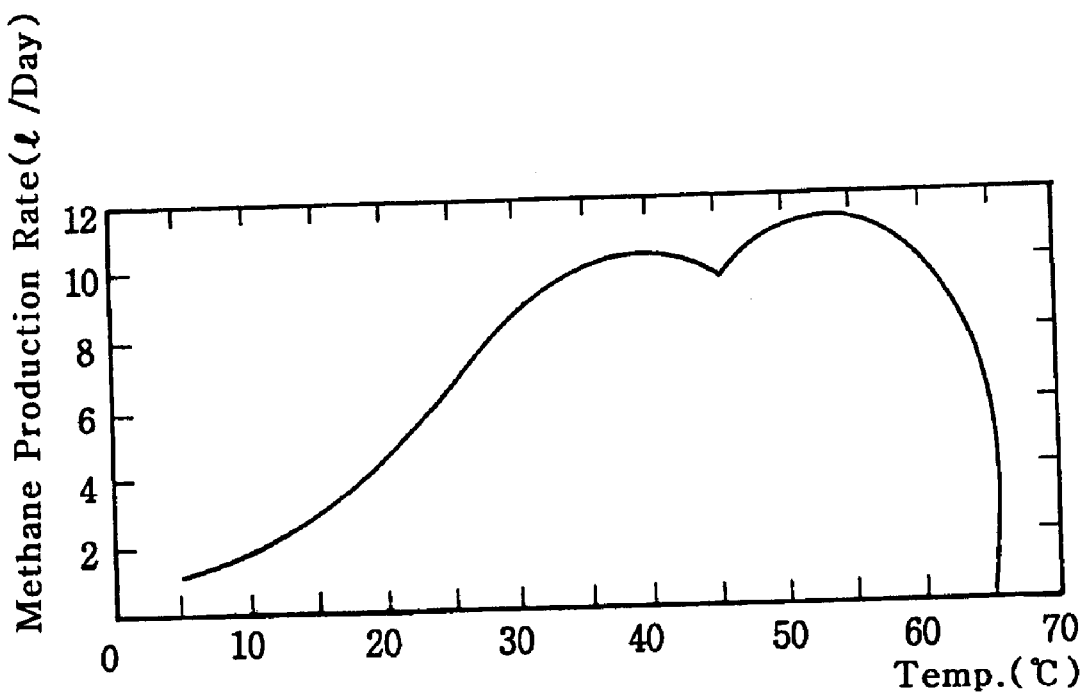
FIG. 4 is a curve showing the change in methane production rate with varying temperatures.
Figure 5:
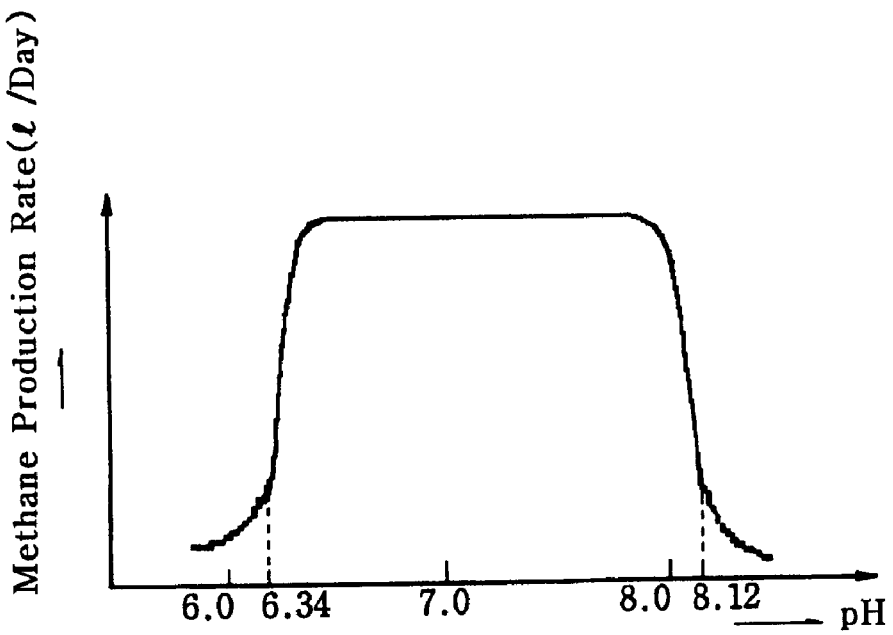
FIG. 5 is a curve showing the change in methane production rate with varying pH.

FIG. 4 is a curve showing the change in the amount of produced methane at varying temperatures. As can be seen in FIG. 4, the amount of produced methane is highly increased at the intermediate temperature range of 35° C. to 38° C. and the higher temperature range of 53° C. and 55° C. Meanwhile, FIG. 5 is a curve showing the change in the amount of produced methane at varying pH. As can be seen in FIG. 5, the amount of produced methane is increased at the pH range of about 6.5 to about 8.0.

As a consequence, in the step (a), the recycling leachate is preferably maintained at the temperature range of 35° C. to 38°. If the recycling leachate is maintained at the higher temperature range of 53° C. to 55° C., the amount of methane generated at an initial stage of the landfilling process may be rapidly increased in excess of the necessary amount. In the case of pH, the maintenance of the recycling leachate at the pH range of 6.5 to 7.5 may result in a great increase in the amount of generated methane gas.

As described above, such a step (a) is carried out until the amount of the generated landfill gas reaches from the range of 5% to 20% of a capability of the landfill gas generation in the landfill. During a period of time between from the termination of the step (a) to the termination of the step (b), the amount of landfill gas generated per one hour is maintained at the level of 50% to 70% of a greatest possible amount of the landfill gas generated per one hour within the landfill. This enables the landfill gas to be stably supplied to the utilization facilities.

The step (b) is the time at which the anaerobic decomposition of the wastes by the methane-producing bacteria is most actively progressing. In this step (b), the amount of generated methane gas is rapidly increased till one year to three years after the completed landfilling, and then gradually decreased. In order to inhibit the increase in the generation rate of the landfill gas and also to maintain the generation rate of the landfill gas at a substantial same level as that of the step (a), the anaerobic condition in the step (b) is somewhat mitigated by monitoring and controlling the temperature and the pH of the leachate recycled to the waste.

As a consequence, in the step (b), the recycling leachate is maintained at the temperature range of 30° C. to 35° C. or the temperature range of 60° C. to 65° C. If the recycling leachate is maintained at the temperatures below 30° C. or above 65° C., the amount of generated methane may be extremly decreased as shown in FIG. 4. Moreover, the recycling leachate is maintained at an increased acidity, namely, the pH range of 6 to 7, compared to the step (a). If the pH of the recycling leachate is below 6, it is problematic in that the amount of generated methane gas is rapidly reduced.

Such a step (b) is carried out until the amount of the generated landfill gas reaches from the range of 75% to 90% of a total amount of the landfill gas capable of being generated in the landfill. Once the step (b) is terminated, the amount of landfill gas generated per one hour is gradually lowered from the level of 50% to 70% of a greatest possible amount of the landfill gas generated per one hour within the landfill.

As described above, after the step (b) is carried out, the step (c) is finally carried out. The time at which the step (c) is carried out is the time at which degradable organic materials contained in the landfilled wastes are remarkably reduced to rapidly decrease the amount of generated landfill gas. Thus, this time is the state in that substrates consumed for the propagation of the methane-producing bacteria are very inactive. Thus, in order to make the anaerobic reaction condition within the landfill an optimized condition, the recycling leachate in the step (c) is maintained at the temperature range of 35° C. to 38° C. or a the temperature range of 50° C. to 54° C. as shown in FIG. 4, and/or at the pH of 6 to 8 as shown in FIG. 5. If necessary, after the methane-producing bacteria of a strong activity are incubated in a bioreactor, the incubated bacteria may be added into the landfilled wastes. This facilitates the decomposition of the degradable organic materials remained within the landfill into methane, thereby stabilizing the landfill over a short period of time.

In such a step (c), to further facilitate the decomposition of the organic materials, it is preferable to seed separately incubated anaerobic degradation microbes in the bioreactor and to recycle the leachate containing the activated anaerobic microbes. This facilitates the decomposition process of the landfill to stabilize the landfill over a short period of time.

Moreover, the present invention relates to an apparatus carrying out the method of controlling the amount of landfill gas generated within the landfill.

Figure 1:
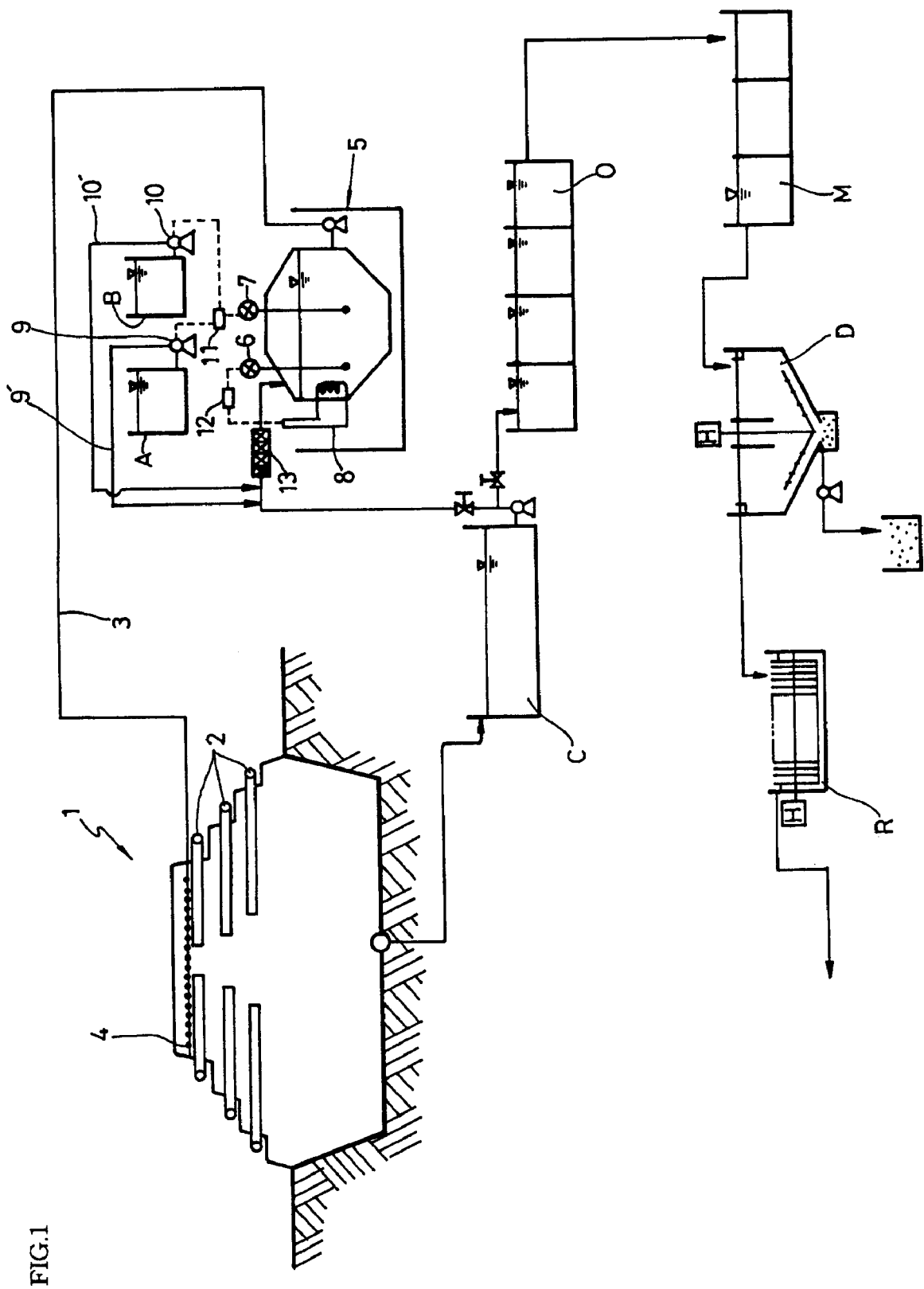
FIG. 1 schematically shows an apparatus of controlling the amount of landfill gas generated within the landfill according to this invention.

FIG. 1 schematically shows an apparatus of controlling the amount of landfill gas generated within the landfill according to this invention.

Referring to FIG. 1, an apparatus of controlling the amount of generated landfill gas according to this invention comprises at least one landfill gas extraction pipe 2 arranged in a landfill 1 and extended to an inner central portion of the landfill 1, and a plurality of leachate injection pipes 4 arranged in such a manner that the leachate is collect at the bottom layer of the landfill 1 and recycled to the upper layer of the landfill 1 through a leachate circulation pipe 3. The leachate circulation pipe 3 is communicated to a bioreactor 5 for monitoring and controlling pH and temperature of the leachate. The bioreactor 5 is equipped with a heating device 8 and a pH sensor 7. Connected to the pH sensor 7 is a pH control transmitter 11. The pH control transmitter 11 serves to control operation of an acid feeding pump 9 and an alkali feeding pump 10. Connected to the temperature sensor 6 is a temperature control transmitter 12 which serves to control operation of the heating device 8. The acid feeding pump 9 and the alkali feeding pump are connected to a line mixer 13 through supplying pipes 9' and 10', respectively.

Also, the apparatus of the invention is provided with a leachate storage tank C. This leachate storage tank C serves to temporally store the leachate collected from the landfill 1, thereby constantly controlling the amount of the leachate introduced into the bioreactor 5. In addition, for a normal purge treatment of the surplus leachate that is effluent from the landfill, the apparatus of the invention is provided with conventional post-treatment devices such as an aeration tank O, a chemical treatment tank M, a sedimentation tank D, and a rotating contact oxidation treatment tank R. Also, the designation A depicts an acidic compound storage tank, and the designation B depicts a basic compound storage tank.

The apparatus described above is operated as follows:

First, the leachate gathered at the bottom of the landfill 1 is collected by the leachate storage tank C, and the suitable amount of the collected leachate is introduced into the bioreactor 5. The introduced leachate is monitored for pH and temperature by the pH sensor 7 and the temperature sensor 6, respectively, included in the bioreactor 5 to determine the pH and the temperature of the leachate at an initial stage of the introduction. The monitored information is transmitted to the pH control transmitter 11 and the temperature control transmitter 12. Based on the information transmitted from the pH sensor 7, the pH control transmitter causes operations of the acid feeding pump 9 connected to the acidic compound storage A, and the alkali feeding pump 10 connected to the basic compound storage tank B, thereby supplying suitable amount of the acidic and basic compounds to the bioreactor 5 through the line mixer 13. This enables the appropriate control of pH of the leachate necessary for the steps (a), (b) and (c) in the method of the invention. Meanwhile, the information obtained by the temperature sensor 6 is transmitted to the heating device 8, thereby enabling the appropriate control of the necessary temperature for the steps (a), (b) and (c) in the method of the invention.

The following examples are for illustration purposes only and in no way limit the scope of this invention.

EXAMPLE 1

Figure 2:
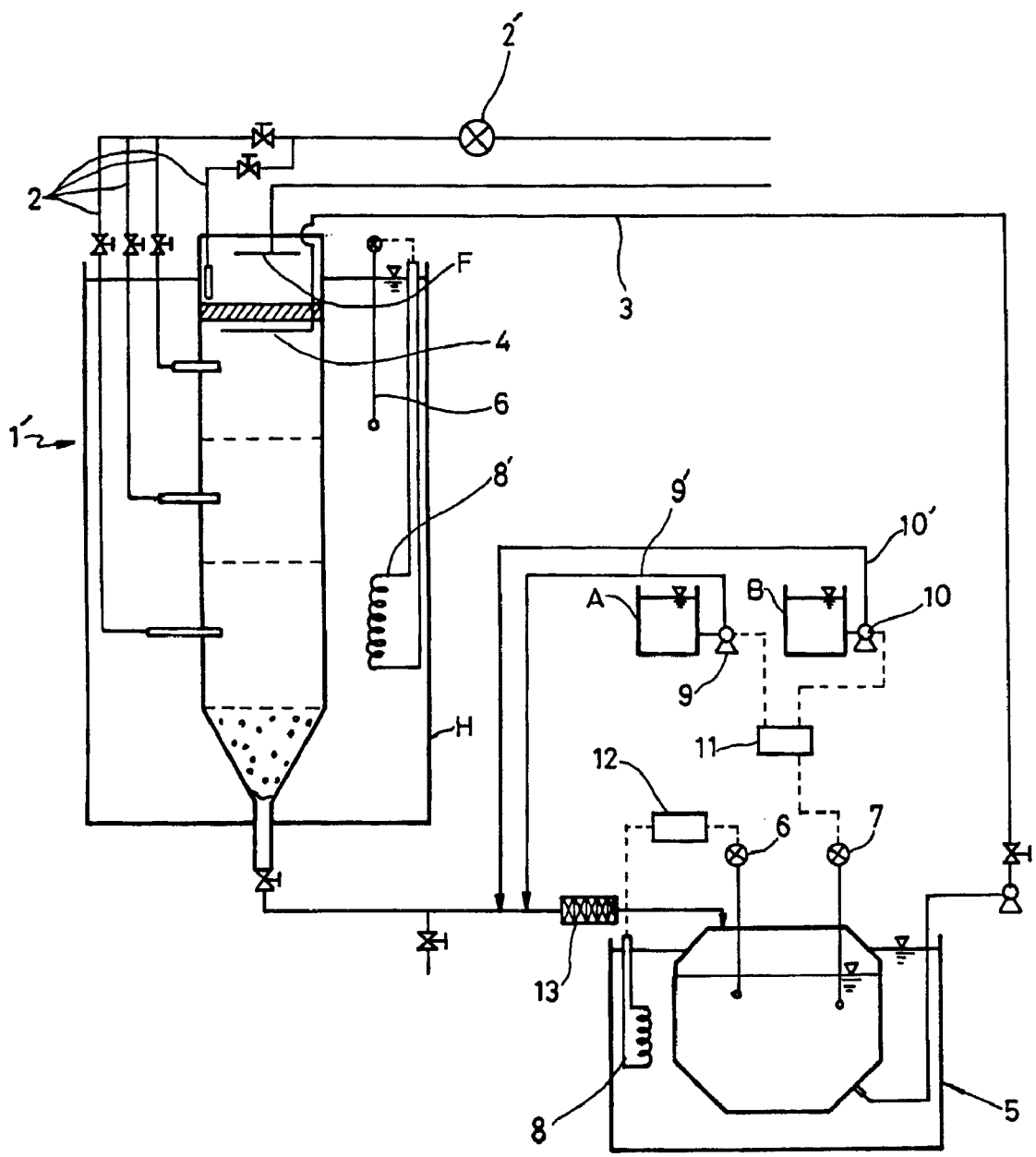
FIG. 2 schematically shows an apparatus of controlling the production rate of landfill gas generated within the landfill according to an experimental example of this invention.

To carry out the landfill gas extraction test according to the inventive method of controlling the amount of the landfill gas generated within the landfill, an apparatus of controlling the amount of the landfill gas shown in FIG. 2 was used. In this case, the used bioreactor has the same construction as that of the bioreactor 5 shown in FIG. 1. As a landfill tank, a simulated landfill tank 1' of a column type was used, having 284 mm in inner diameter, 1,800 mm in height, and 1,300 mm in burying depth. On the exterior of the tank 1', there was disposed a warming tank H equipped with a temperature sensor 6' and a heating device 8' operated by the temperature sensor 6'. Additionally, an artificial rainfall device F was disposed on the top of the tank 1'. Also, a gauge 2' for measuring the extracted gas amount was disposed at a desired point of a landfill gas extraction pipe 2.

A waste column sample used in this example was taken from an apartment development, in Inchon, Korea. The physical composition of the sample was as follows:

Foods 56.74%; Papers 18.75%; Woods 0.95%; Plastics 2.47%; Rubbers 0.10%; Leathers 0.15%; Fibers 1.29%; Vinyls 14.21%; Metals 1.64%; Nonmetals 0.72%; Glasses 2.53%; and Ceramics 0.45%.

The chemical composition of the sample after drying was as follows:

C 45.98%; H 6.97%; O 27.21%; N 2.74%; S 0.40%; Cl 0.32%; and ashes 16.38%.

55 Kg of the waste was filled into a column of the simulated landfill tank 1' and the leachate was then recycled for a period of time of 300 days. In this case, by controlling the pH sensor 7 and the temperature sensor 6, the leachate were maintained at the pH of 7.5 and at the temperature range of 35 to 37° C. This control was continued for 70 days at a daily landfill gas emission amount of 0.7 liter/day corresponding to a 70% level of 1 liter/day, an estimated value of a greatest possible emission amount.

At 71 days after starting the recycling of the leachate, the temperature of the leachate was controlled at the temperature range of 31 to 33° C. and the pH of 6.3. This control of the leachate was maintained until 250 days after starting the recycling of the leachate. During this control period, the daily landfill gas emission amount slowly increased to a peak of 0.9 liter/day, and decreased from 0.9 liter/day, and then returned to a 70% level of 1 liter/day, an estimated value of a greatest possible emission amount, at 250 days after starting the recycling of the leachate.

At 251 days after starting the recycling of the leachate, the leachate was controlled to at the temperature range of 52 to 54° C. and the pH of 7.8. This control of the leachate was continued till 300 days after starting the recycling of the leachate. Thus, the total amount of the emitted landfill gas reached near 100% level of the total amount of the landfill gas capable of being emitted from the buried waste. After 300 days, the landfill gas was not substantially generated.

Figure 6:
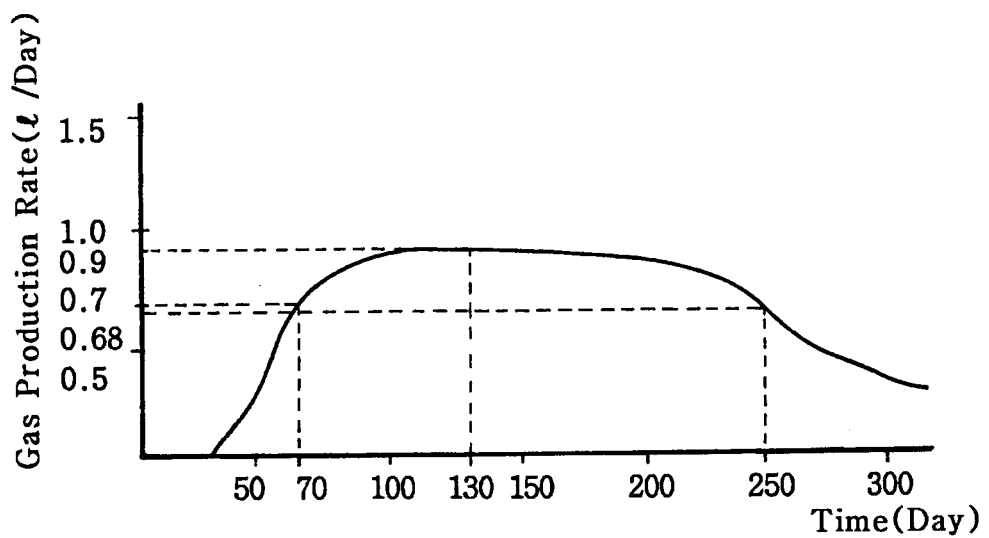
FIG. 6 is a curve showing the amount of landfill gas generation during the according to Example 1 of the invention.

FIG. 6 is a curve showing the change in the amount of the generated landfill gas with varying times during the burying process. In the burying stage, the temperature of the warming tank H was consistent with the temperature of the leachate.

EXAMPLE 2

The procedure described in the above example 1 was repeated. However, 80 Kg of wastes which have been landfilled for six years were used in this example. The physical composition of the wastes was as follows:

Foods, not measured; Papers, not measured; Woods, 5.12%; Plastics, 0.10%; Rubbers, not measured; Leathers, not measured; Fibers, 0.31%; Vinyls, 0.45%; Metals, 2.24%; Nonmetals, not measured; and Ceramics, 3.51%, Glasses 3.51%.

After drying, the chemical composition of the waste was as follows:

C 6.12%; H 0.68%; O 5.32%; N 0.19%; S 0.52%; Cl 1.21%; and ashes 85.96%.

Figure 7:
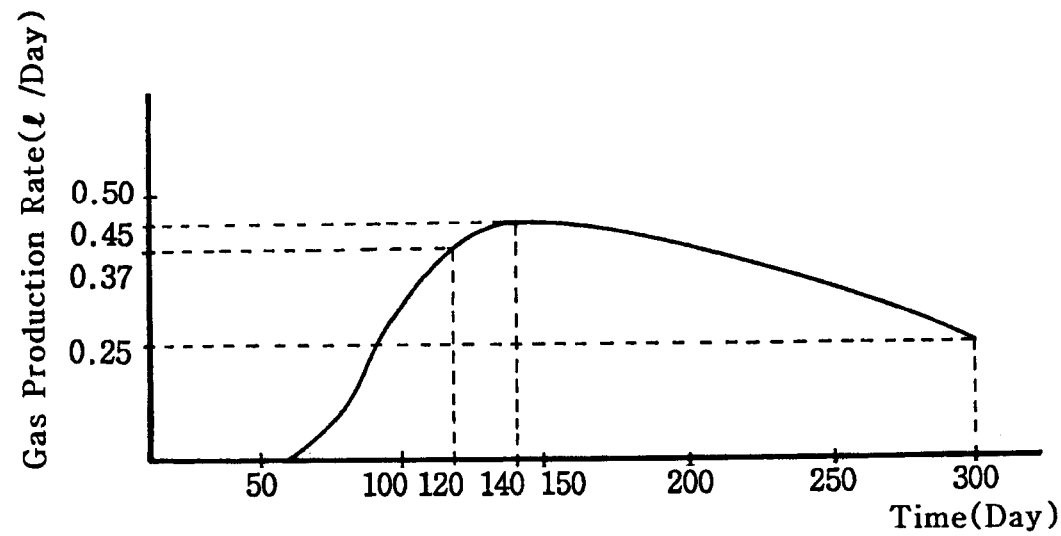
FIG. 7 is a curve showing the amount of landfill gas generation during the burying process according to Example 2 of the invention.

Such wastes were in the state in which the anaerobic condition was greatly lowered, due to oxygen introduced into the wastes for the delivery process. For this reason, before filling into the waste burying column, the wastes were mixed with the methane-producing bacteria and then incubated for 120 days. After that, the recycling leachate was continuously maintained at the temperature range of 31 to 33° C. and the pH of 6.3. FIG. 7 is a curve showing the amount of landfill gas generated during the burying process of the wastes in this example.

Comarative Example 1

Figure 8:
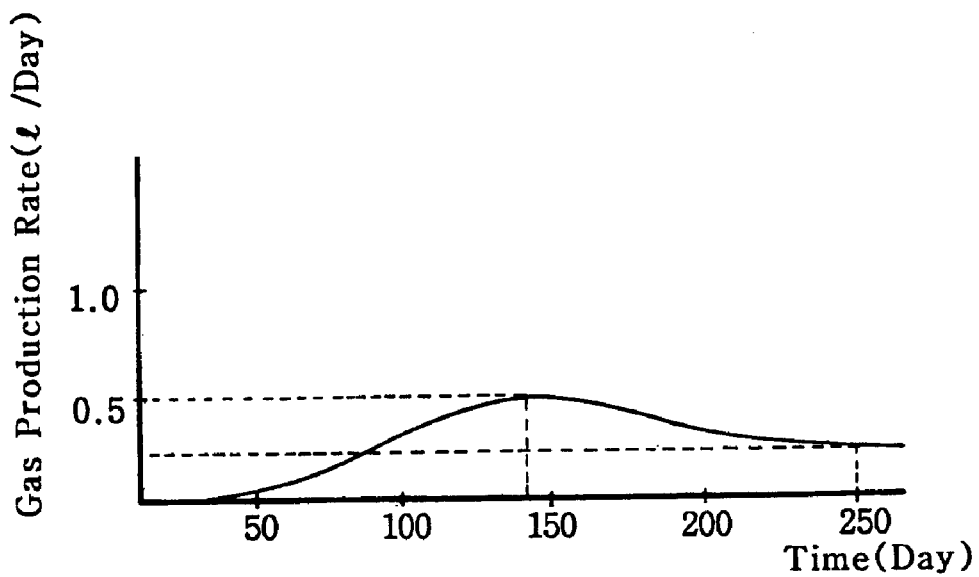
FIG. 8 is a curve showing the amount of landfill gas generation during the burying process according to Comparative Example 1.

The procedure described in the above Example 1 was repeated. However, the bioreactor 5 was not operated, and the leachate was not recycled. FIG. 8 is a curve showing the amount of landfill gas generated during the burying of the wastes in this comparative example.

Comarative Example 2

Figure 9:
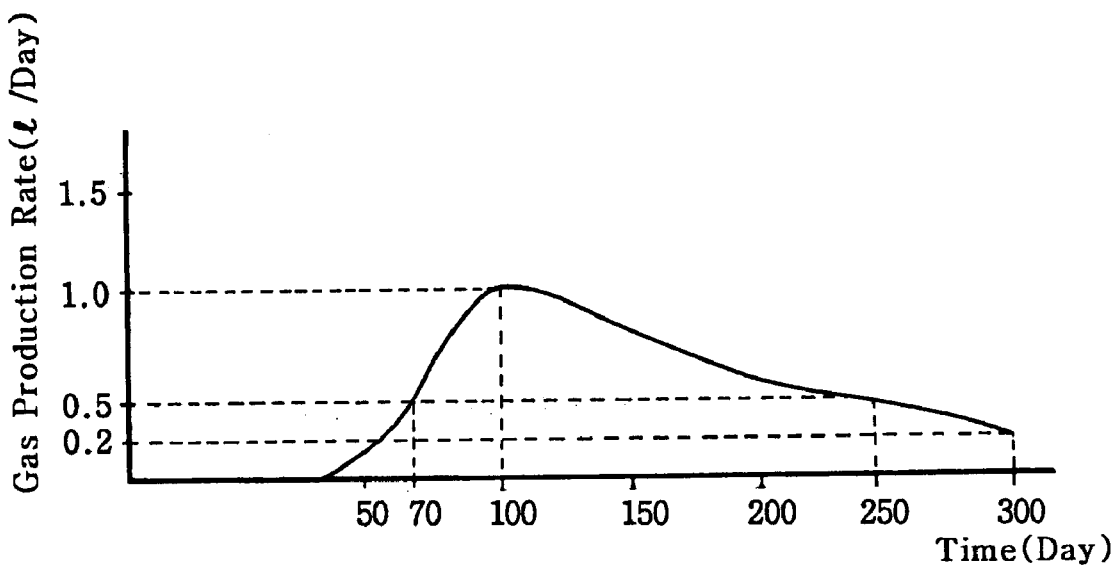
FIG. 9 is a curve showing the amount of landfill gas generation during the burying process according to Comparative Example 2.

The procedure described in the above Example 1 was repeated. However, the bioreactor 5 was not operated, and the leachate was continuously recycled. FIG. 9 is a curve showing the amount of landfill gas generated during the burying of the wastes in this comparative example.

Comarative Example 3

Figure 10:
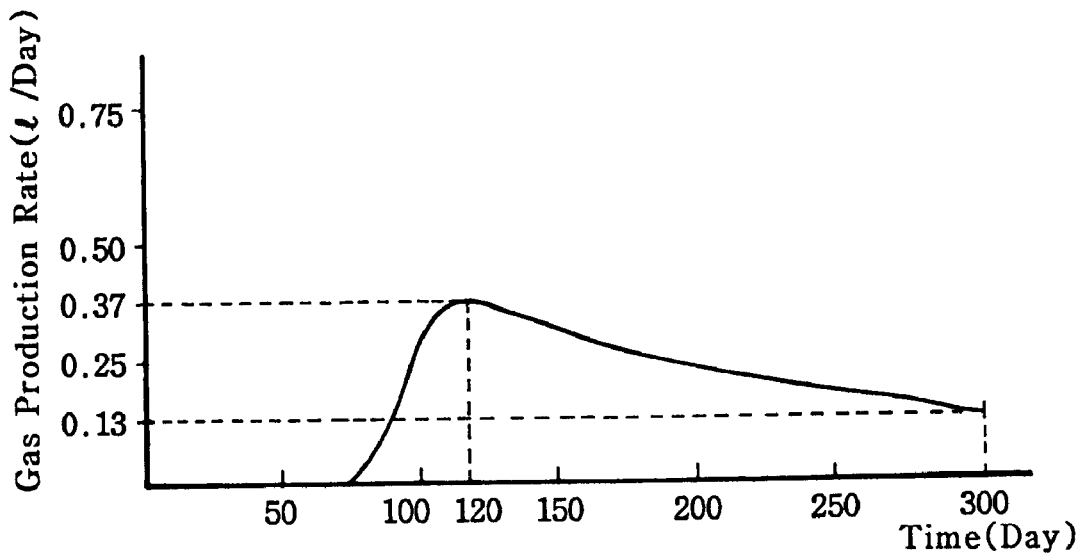
FIG. 10 is a curve showing the amount of landfill gas generation during the burying process according to Comparative Example 3.

The procedure described in the above Example 2 was repeated. However, the bioreactor 5 was not operated, and the leachate was continuously recycled. FIG. 10 is a curve showing the amount of landfill gas generated during the burying of the wastes in this comparative example.

As can be learned from FIGS. 6, 8 and 9, in the Example 1 of this invention, the daily average generation rate of the landfill gas is at 0.7 liter/day for 70 days after burying (corresponding to the step (a) of the invention). Thus, the anaerobic reaction at the initial stage of the burying process is rapidly facilitated to greatly increase the methane gas production reaction rate.

Moreover, from 70 days to 250 days (corresponding to the step (b) of the invention) after burying the wastes, the daily generation rate of the landfill gas shows less variation with respect to the daily average rate of 0.9 liter/day of the landfill gas generated at 130 days after burying. From this fact, it is confirmed that a variety of facilities using the landfill gas can be designed and constructed at a reasonable scale, and an efficiency for extracting and utilizing the landfill gas containing an amount of methane gas useful as the energy source can thus be maximized.

On the other hand, in the case of the Comparative Example 1 in which the recycling of the leachate is not carried out, the generation of the landfill gas by the degradation of the organic material is very slowly progressed as shown in the curve of FIG. 8. Moreover, at the initial stage of the organic material degradation, the landfill gas does not substantially contain methane gas as the aerobic degradation is almost predominant. In addition, a great variation in the generated amount of the landfill gas during the burying process does not provide the desirable results of being highly economical.

In the case of the Comparative Example 2, it is advantageous in that the amount of generated methane gas can be increased, as shown in FIG. 9, by recycling the leachate at the initial stage of the burying process to inhibit the aerobic degradation and to facilitate the anaerobic environment. However, as a variation in the generated amount of the landfill gas during the burying process is great, a variety of facilities using the landfill gas are difficult to design. Thus, a proportion of the lost landfill gas is increased to greatly lower an efficiency for utilizing the landfill gas. Moreover, even after the burying process for 300 days, about 0.2 liter/day of gas is continuously generated and the initial stabilization effect of the landfill cannot be thus achieved.

In the case of the Example 2 of this invention (FIG. 7) using the wastes which had been buried for six years, even after the wastes are buried for 120 days according to the Example 2, the daily everage generation rate of landfill gas is continuously increased until 140 days at which the daily average rate landfill gas generation reaches 0.45 liter/day. Then, the daily average rate of landfill gas generation is reduced until 300 days. Thus, as the carbon nutrient source during this burying process is rapidly consumed, it is expected that the daily average rate of landfill gas generation is rapidly decreased after 300 days. As a consequence, according to this invention, an amount of the landfill gas can be generated during the unit term, such that an efficiency of the facilities utilizing such a landfill gas is maximized and also the initial stabilization effect is remarkably improved.

However, in the case of the Comparative Example 3 (FIG. 10), the daily average rate of landfill gas generation is rapidly reduced from a peak of 0.37 liter/day at 140 days after the burying of the wastes. For this reason, in the Comparative Example 3, the daily average rate of landfill gas generation, compared to that of the Example 1, is much less for a period of the same time to unavoidably greatly lower the landfill gas and the facility using the landfill gas. In addition, as a nondegraded carbon nutrient source largely remains in the wastes, the time required for the stabilization of the landfill is delayed.

INDUSTRIAL APPLICABILITY

The present invention appropriately monitors and controls a variety of conditions of the recycling leachate for each of processes including a landfilling process, a post-landfilling process and a landfilling stabilization process, such that the amount of the landfill gas generated is kept as constant as possible throughout all these processes. This enables the design of facilities utilizing the landfill gas, such as purification equipment and a power generation facility, at an reasonable scale. Therefore, the present invention enables the cost of the investment in the facilities to be recovered over a short period of time, the utilization efficiency of the landfill gas resource to be maximized, and also the landfill to be stabilized over a short period of time.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method of controlling an amount of landfill gas generated in a landfill, in which leachate is recycled to be continuously injected into a deposit of wastes while extracting the landfill gas from a landfill gas extraction pipe inserted into the waste deposit, comprising the steps of:

(a) maintaining the recycling leachate at a temperature range of 35° C. to 38° C. and a pH of 6.5 to 7.5 until the amount of generated landfill gas reaches a range of 5% to 20% of a maximum landfill gas generation capability in the landfill;

(b) maintaining the recycling leachate at a temperature range of 30° C. to 35° C. and a pH of 6 to 7 until the amount of generated landfill gas reaches a range of 75% to 90% of the maximum landfill gas generation capability in the landfill;

(c) maintaining the recycling leachate at a temperature range of 35° C. to 38° C. and a pH of 6.5 to 8.0 until the amount of generated landfill gas reaches 100% of a the maximum landfill gas generation capability in the landfill.

2. The method according to claim 1, wherein the step (c) further comprises seeding separately incubated anaerobic microbes in the recycling leachate.

3. The method according to claim 1, wherein the step (a) is performed for approximately 70 days. the step (b) is performed for approximately 180 days, and the step (c) is performed for approximately 50 days.

4. The method according to claim 1, wherein the deposit of wastes includes at least two of food, paper, wood, plastic, rubber, leather, fiber, vinyl, metal, glass and ceramic.

5. An apparatus for controlling the amount of generated landfill gas comprising:

at least one landfill gas extraction pipe arranged in a landfill and extended to an inner central portion of the landfill, said landfill having a bottom layer and an upper layer;

a plurality of leachate injection pipes arranged in such a manner that the leachate is collected at the bottom layer of and recycled to the upper layer of the landfill through a leachate circulation pipe;

a bioreactor for monitoring and controlling a pH and a temperature of the leachate, the bioreactor being communicated with the leachate circulation pipe and equipped with a heating device, a temperature sensor and a pH sensor;

a pH control transmitter connected to the pH sensor to control operation of an acid feeding pump and an alkali feeding pump, a pump system of the acid feeding pump and the alkali feeding pump connected to a line mixer; and a temperature control transmitter connected to the temperature sensor to control the operation of the heating device.

6. A method of controlling an amount of landfill gas generated in a landfill, in which leachate is recycled to be continuously injected into a deposit of wastes while extracting the landfill gas from a landfill gas extraction pipe inserted into the waste deposit, comprising the steps of:

(a) maintaining the recycling leachate at a temperature range of 35° C. to 38° C. and a pH of 6.5 to 7.5 until the amount of generated landfill gas reaches a range of 5% to 20% of a maximum landfill gas generation capability in the landfill;

(b) maintaining the recycling leachate at a temperature range of either 30° C. to 35 ° C. or 60° C. to 65° C. until the amount of generated landfill gas reaches a range of 75% to 90% of the maximum landfill gas generation capability in the landfill;

(c) maintaining the recycling leachate at a temperature range of either 35° C. to 38° C. or 50° C. to 54° C. until the amount of generated landfill gas reaches 100% of the maximum landfill gas generation capability in the landfill.

7. The method as set forth in claim 6 wherein the temperature range in step (b) is 30° C. to 35° C.

8. The method as set forth in claim 7 wherein, in step (b), the recycling leachate is maintained at a pH of 6 to 7.

9. The method as set forth in claim 6 wherein the temperature range in step (b) is 60° C. to 65° C.

10. The method as set forth in claim 9 wherein, in step (b), the recycling leachate is maintained at a pH of 6 to 7.

11. The method as set forth in claim 6 wherein the temperature range in step (c) is 35° C. to 38° C.

12. The method as set forth in claim 11 wherein, in step (c), the recycling leachate is maintained at a pH of 6.5 to 8.

13. The method as set forth in claim 6 wherein the temperature range in step (c) is 50° C. to 54° C.

14. The method as set forth in claim 13 wherein, in step (c), the recycling leachate is maintained at a pH of 6.5 to 8.

15. The method as set forth in claim 6 wherein the temperature range in step (b) is 30° C. to 35° C. and the temperature range in step (c) is 35° C. to 38° C.

16. The method as set forth in claim 6 wherein the temperature range in step (b) is 30° C. to 35° C. and the temperature range in step (c) is 50° C. to 54° C.

17. The method as set forth in claim 6 wherein the temperature range in step (b) is 60° C. to 65° C. and the temperature range in step (c) is 35° C. to 38° C.

18. The method as set forth in claim 6 wherein the temperature range in step (b) is 60° C. to 65° C. and the temperature range in step (c) is 50° C. to 54° C.

19. The method according to claim 6, wherein the step (c) further comprises seeding separately incubated anaerobic microbes in the recycling leachate.

20. The method according to claim 6, wherein the deposit of wastes includes at least two of food, paper, wood, plastic, rubber, leather, fiber, vinyl, metal, glass and ceramic.

\* \* \* \* \*